United States Patent
Lechot et al.

(10) Patent No.: US 10,022,089 B2
(45) Date of Patent: Jul. 17, 2018

(54) MEASURING DEVICE FOR DETERMINING CEREBRAL PARAMETERS

(71) Applicant: Luciole Medical AG, Zurich (CH)

(72) Inventors: Christophe Lechot, Biel (CH); Jean-Claude Frely, Biel (CH); Marcel Aeschlimann, Ligerz (CH); Juerg Hans Froehlich, Zurich (CH); Dirk Baumann, Zurich (CH); Markus Hugo Muser, Waedenswil (CH); Michael Oberle, Zurich (CH)

(73) Assignee: Luciole Medical AG, Zurich (CH)

( * ) Notice: Subject to any disclaimer, the term of this patent is extended or adjusted under 35 U.S.C. 154(b) by 406 days.

(21) Appl. No.: 14/437,712

(22) PCT Filed: Nov. 1, 2013

(86) PCT No.: PCT/EP2013/072870
§ 371 (c)(1),
(2) Date: Apr. 22, 2015

(87) PCT Pub. No.: WO2014/072231
PCT Pub. Date: May 15, 2014

(65) Prior Publication Data
US 2015/0282762 A1    Oct. 8, 2015

(30) Foreign Application Priority Data

Nov. 6, 2012  (CH) ...................... 2266/12

(51) Int. Cl.
*A61B 5/1455*  (2006.01)
*A61B 5/00*  (2006.01)

(52) U.S. Cl.
CPC ........ *A61B 5/6833* (2013.01); *A61B 5/14552* (2013.01); *A61B 5/14553* (2013.01);
(Continued)

(58) Field of Classification Search
CPC .............. A61B 5/1455; A61B 5/14551; A61B 5/14552; A61B 5/14553; A61B 5/14532;
(Continued)

(56) References Cited

U.S. PATENT DOCUMENTS 4,730,622 A   3/1988   Cohen
4,986,671 A   1/1991   Sun et al.
(Continued)

FOREIGN PATENT DOCUMENTS

EP   0481612 A1   4/1992
EP   0933061 B1   10/2004
(Continued)

OTHER PUBLICATIONS

Di Ieva, Antonio, et al., "Analysis of Intracranial Pressure Past, Present, and Future", *The Neuroscientist*, Feb. 6, 2013, pp. 592-603, vol. 19, Issue 6, SAGE Publications Inc, U.S.A.
(Continued)

*Primary Examiner* — Eric Winakur
*Assistant Examiner* — Chu Chuan (JJ) Liu
(74) *Attorney, Agent, or Firm* — Alston & Bird LLP

(57) ABSTRACT

The invention relates to a device and a method for noninvasive measurement of parameters of a bodily tissue, the measuring device having a sensor unit and a sensor mat for detachable placement of the device on a body surface. The sensor unit (1) has a receptacle (6), the interior of which accommodates a sensor arrangement, wherein the receptacle (6) has a sensor surface (15) in the direction of the body surface. The sensor mat (8) has a cutout (11) for accommodating the sensor unit (1) and a contact surface (14), at least partially surrounding the sensor unit (1), for placement on the body surface (9). A cover (12) is provided for closing the cutout (11) over an upper side of the sensor unit (1) and the sensor mat (8) during a measurement of parameters. The
(Continued)

sensor unit (1), the sensor mat (8) and the cover (12) are detachable from one another.

17 Claims, 2 Drawing Sheets

(52) U.S. Cl.
CPC .... *A61B 5/6832* (2013.01); *A61B 2560/0412* (2013.01); *A61B 2560/0443* (2013.01); *A61B 2562/0238* (2013.01); *A61B 2562/164* (2013.01)

(58) Field of Classification Search
CPC ............ A61B 2562/00; A61B 2562/02; A61B 2562/0233; A61B 5/6832; A61B 5/6833; A61B 2560/0412; A61B 2560/0443; A61B 2562/164; A61B 2562/0238
See application file for complete search history.

(56) References Cited

U.S. PATENT DOCUMENTS

| | | | |
|---|---|---|---|
| 5,090,410 | A | 2/1992 | Saper et al. |
| 5,579,774 | A | 12/1996 | Miller et al. |
| 5,706,821 | A | 1/1998 | Matcher et al. |
| 5,879,373 | A * | 3/1999 | Roper ............... A61B 5/14552 600/322 |
| 6,029,671 | A | 2/2000 | Stevens et al. |
| 6,195,574 | B1 | 2/2001 | Kumar et al. |
| 6,261,226 | B1 | 7/2001 | McKenna et al. |
| 6,315,712 | B1 | 11/2001 | Rovegno |
| 6,373,567 | B1 | 4/2002 | Wise et al. |
| 6,447,527 | B1 | 9/2002 | Thompson et al. |
| 6,608,684 | B1 | 8/2003 | Gelikonov et al. |
| 7,047,054 | B2 | 5/2006 | Benni |
| 8,190,229 | B2 * | 5/2012 | Lowery ............... A61B 5/6833 600/323 |
| 2001/0002250 | A1 | 5/2001 | Burbank et al. |
| 2001/0038063 | A1 | 11/2001 | Mitsuoka et al. |
| 2002/0095087 | A1 | 7/2002 | Mourad et al. |
| 2003/0032915 | A1 | 2/2003 | Saul |
| 2003/0071988 | A1 | 4/2003 | Smith et al. |
| 2004/0019293 | A1 | 1/2004 | Schweitzer et al. |
| 2004/0199063 | A1 * | 10/2004 | O'Neil ............... A61B 5/14552 600/344 |
| 2005/0043596 | A1 | 2/2005 | Chance |
| 2005/0165303 | A1 | 7/2005 | Keen et al. |
| 2007/0019916 | A1 | 1/2007 | Takami |
| 2007/0167867 | A1 | 7/2007 | Wolf |
| 2008/0143822 | A1 | 6/2008 | Wang et al. |
| 2008/0208011 | A1 | 8/2008 | Shuler |
| 2012/0071742 | A1 * | 3/2012 | Medina ............... A61B 5/14552 600/344 |
| 2012/0136240 | A1 | 5/2012 | Pranevicius et al. |

FOREIGN PATENT DOCUMENTS

| | | |
|---|---|---|
| EP | 1301119 B1 | 6/2005 |
| EP | 2294973 A2 | 3/2011 |
| JP | H07-294519 A | 11/1995 |
| JP | 2002-010986 A | 1/2002 |
| JP | 2002-509453 A | 3/2002 |
| JP | 2008-067914 A | 3/2008 |
| JP | 2008-279274 A | 11/2008 |
| JP | 2010-520773 A | 6/2010 |
| WO | WO 1994/027494 A1 | 12/1994 |
| WO | WO 1998/08434 A1 | 3/1998 |
| WO | WO 1999/037204 A1 | 7/1999 |
| WO | WO 2001/040776 A1 | 6/2001 |
| WO | WO 2005/082225 A1 | 9/2005 |
| WO | WO 2007/064984 A2 | 6/2007 |
| WO | WO 2007/132868 A1 | 11/2007 |
| WO | WO 2009/062189 A1 | 5/2009 |
| WO | WO 2010/015094 A2 | 2/2010 |

OTHER PUBLICATIONS

Fan, J.Y., et al., "Intracranial Pressure Waveform Morphology and Intracranial Adaptive Capacity", *American Journal of Critical Care*, Nov. 2008; pp. 545-554, vol. 17, No. 6., The American Association of Critical-Care Nurses, U.S.A.

Raksin, Patricia B., et al., "Noninvasive Intracranial Compliance and Pressure Based on Dynamic Magnetic Resonance Imaging of Blood Flow and Cerebrospinal Fluid Flow", *Neurosurg Focus*, 2003, 13 pages, vol. 14, No. 4, retrieved from <http://www.medscape.com/viewarticle/452769_print> on Oct. 30, 2015.

Themelis, George, et al. "Near-Infrared Spectroscopy Measurement of the Pulsatile Component of Cerebral Blood Flow and Volume from Arterial Oscillations", *Journal of Biomedical Optics*, Jan. 2007, pp. 014033-1 to 014033-7, vol. 12, Issue 1, International Society for Optics and Photonics, U.S.A.

International Searching Authority, International Search Report (ISR) and Written Opinion for International Application No. PCT/EP2013/072870, dated Feb. 18, 2014, 14 pages, European Patent Office, The Netherlands.

Japan Patent Office, Search Report for Application No. 2016-514389, dated Dec. 5, 2016, 18 pages, Japan.

* cited by examiner

MEASURING DEVICE FOR DETERMINING CEREBRAL PARAMETERS

CROSS REFERENCE TO RELATED APPLICATIONS

This application is a national stage application, filed under 35 U.S.C. § 371, of International Application No. PCT/EP2013/072870 filed Nov. 1, 2013, which claims priority to Swiss Application No. 02266/12 filed Nov. 6, 2012, the contents of both of which as are hereby incorporated by reference in their entirety.

BACKGROUND

Technical Field

This invention relates to a measuring device and a method for measuring parameters of a bodily tissue with a sensor unit and a sensor pad for attaching to the bodily tissue, in particular a non-invasive measuring device and a non-invasive method for measuring cerebral parameters, such as e.g. the oxygen concentration of the brain.

Description of Related Art

Diverse non-invasive methods for cerebral diagnostics are known in which diverse cerebral parameters are measured. For example, parameters are measured relating to the concentration deoxygenated and oxygenated hemoglobin, the cerebral blood flow or the tissue oxygen index. To capture these parameters e.g. a measuring device can be placed on a head surface, preferably on the forehead, and measurements on the brain surface can thereby be carried out. Belonging to methods of this kind is e.g. near-infrared spectroscopy (NIRS).

Known from EP 2294973 A2 is, for example, a pulse oximetry sensor which has an annular contact support for placement on a body surface and a sensor body which is received in an opening of the contact support. The sensor body is firmly connected to the contact support, but can however be moved relative thereto, i.e. swung open in order to make accessible the lower side of the sensor body when the contact support is attached to the body surface. For this purpose a hinge connection is provided between the contact support and the sensor body. The sensor body has a slightly flexible optical mount for receiving an emitter and a detector, the detector being disposed at a fixed spacing apart from the emitter. The emitter and the detector are connected to a patient contact surface of the sensor body. Disposed on the patient contact surface are a multiplicity of stacked individually removable adhesive layers which adhere to a body surface of a patient and are used one after the other. A used adhesive layer can thereby be pulled off and disposed of while the pulse oximetry sensor with the next adhesive layer can be placed again on the body surface.

Furthermore known from U.S. Pat. No. 7,047,054 is a reusable NIRS monitoring assembly for non-invasive monitoring of blood oxygen concentration with which the energy level and the magnitude of a laser field on a body surface is controlled and with which the noise ratio between laser light and detector can be improved through an EMI shield. Adhesion elements are used which are disposed on the reusable monitoring assembly in order to attach the monitoring assembly to a body surface. The adhesion elements are removable and are disposed of after a measurement.

With measurement setups according to the state of the art a tedious cleaning is often necessary in order to make them ready for the next measurement after a measurement has been carried out. Or single-use setups are used. With measurement setups having a multiplicity of elements which are supposed to come to lie on the body surface during a measurement, it can happen that the contact of emitters and detectors on the body surface is undefined or uneven and the measurement results are thereby affected in a disadvantageous way.

BRIEF SUMMARY

It is an object of the present invention to provide a non-invasive measuring device and a non-invasive method for measuring parameters of a bodily tissue in which the handling of the device and its construction is simplified, the costs for carrying out measurements are reduced, and the precision of measurements improved. In particular a homogeneous contact between the measuring device and a surface of the bodily tissue should be ensured.

This and further objects are achieved by a non-invasive measuring device and a method for preparing such a measuring device according to the independent claims. Special embodiments and/or variants follow from the subordinate claims.

A measuring device for non-invasive measurement of parameters of a bodily tissue according to the present invention has a sensor unit and a sensor pad for detachable attachment, or respectively for fixing, of the measuring device, in particular the sensor unit, to a body surface.

The sensor unit has a receptacle, e.g. of silicon, which receives in its interior space a sensor arrangement. The receptacle is designed, for example, as flat, substantially elongated housing and has on a lower side a measuring surface in direction of the body surface. In the measuring surface one or more passages or windows can be provided which make possible a passage of light into and out of the receptacle. An upper side of the receptacle can be completely or partially open in order e.g. to mount the sensor arrangement therein. If the sensor arrangement is accommodated inside the receptacle, the upper side can be closed, e.g. with a foil or a lid. A lightproof closing cover is preferably used in order to prevent incoming extraneous light. The closing cover can be formed preferably by means of a sealing which seals the sensor arrangement in the interior space of the receptacle. Black silicon can be used, for example, for this purpose. The sensor unit thus forms a compact unit closed on all sides with flat surfaces. The sensor arrangement comprises a multiplicity of elements. It comprises at least the outlets of one or more light sources, such as laser diodes, one or more light sources themselves, one or more sensor surfaces, or respectively sensors, which are preferably provided at a spacing apart from the light sources, as well as optical, or respectively electrical, conductors, which transport e.g. light of the light source or sources or light received from the sensor surfaces or electrical signals from and to the elements of the sensor arrangement. Further elements can be provided in the receptacle, such as e.g. a control unit, as will be described in the following. Preferably provided as light sources are at least four different laser diodes of differing wavelength, which can be switched on and off at staggered times. The elements of the sensor arrangement are preferably accommodated completely inside the receptacle, i.e. they do not protrude beyond the receptacle.

The sensor pad has an inner cutout or a passage for receiving the sensor unit. Preferably the shape of the cutout, or respectively of the passage, is adapted to the outer shape of the receptacle. The receptacle thereby fits with its peripheral surface in a precisely fitted way in the sensor pad and forms therewith a form fit. The sensor pad further comprises an at least partially encircling lower contact surface for placement on the body surface. Preferably the contact surface of the sensor pad surrounds the sensor unit completely and thus runs in an encircling way around the sensor unit. The contact surface of the sensor pad in the area in which it surrounds the sensor unit is at least 4 mm, preferably at least 5 mm, wide, so that it protrudes laterally from the periphery of the receptacle of the sensor unit by at least these 5 mm.

Further provided is a covering over an upper side of sensor unit and sensor pad for closing of the cutout or respectively passage during a measurement of parameters. Preferably the covering covers the entire upper side of the sensor pad. The surface of the covering therefore corresponds substantially to the extent of the upper side of the sensor pad (8). A closed-pore foam material serves e.g. as covering.

The sensor unit can be held in the sensor pad e.g. by means of a formfitting and/or frictionally engaged connection. It can also be held in the cutout by the covering on the upper side and a closure on the lower side.

According to the invention the sensor unit, the sensor pad and the covering are provided in a way detachable from one another. This means that they are connected together in such a way that at least the sensor unit can be detached in a non-destructive way from the sensor pad and the covering. The connecting or holding means for assembling sensor unit, sensor pad and covering enable a simple removal of the covering from sensor pad and sensor unit and removal of the sensor unit out of the sensor pad. For this purpose sensor unit, sensor pad and covering are provided as elements to be assembled of a kind of kit, which can be put together e.g. by a medical specialist for preparation of the measuring device for a measurement of body parameters. The sensor unit can thereby be provided as reusable unit. After a measurement it can be cleaned and made available for a further measurement. The sensor pad and the covering can be provided as single-use units, i.e. after being removed from the body surface after a measurement they should be disposed of. After a measurement, the elements of the kit, i.e. the sensor mat, the sensor unit and the covering can be detached again from one another, or respectively removed from one another. The measuring device of the present invention can therefore be made available in an inexpensive way and can be made ready for a parameter measurement in a simple, uncomplicated way.

An adhesive layer can be provided over a lower side of sensor unit and sensor pad for attachment of the measuring device for measuring parameters of a bodily tissue on the body surface. The adhesive layer is preferably designed to be transparent in order to ensure a passage of light into and out of the sensor unit. The adhesive layer ensures the contact between the sensor pad and the sensor unit, and forms a sterile barrier between the body surface and the measuring device.

Since the sensor unit in assembled state abuts the covering with its upper side, the sensor unit is pressed with its lower side, on which are located the outlets of the light source or sources and the sensor surfaces, against the body surface. A good contact between body surface and measuring surface is thereby established. Furthermore a reliable beaming of the emitted light into the bodily tissue and receiving of light to be measured on the sensor surfaces is ensured. A signal-to-noise ratio can thereby be improved and the quality increased of the measurement results for the parameters to be measured. The measuring surface and the contact surface thereby lie preferably in one plane in order to prevent an excessive pressing of the sensor unit into the body surface. The bodily tissue is thereby affected by the sensor unit as little as possible, and the blood supply is not influenced in the region of the measuring device.

In an embodiment of the measuring device according to the present invention the receptacle abuts an inner side of the covering, as mentioned above. Accordingly the receptacle not only adjoins the covering, but the covering serves in fact as a stop and blocks a movement of the sensor unit in direction of the covering relative to the sensor pad. In assembled state of the measuring device the sensor pad and the receptacle are therefore fixed with respect to one another in this direction. In a state of the measuring device being put on a body surface, the covering of the sensor pad presses the receptacle of the sensor unit and thereby the sensor surfaces and the outlets of the light source or sources against the body surface, as mentioned above. The adhesive layer can serve on the undersurface of the sensor pad as fixation for the sensor unit inside the cutout.

Preferably the sensor pad is designed flexible or bendable. Upper and lower side, in particular the contact surface, are therefore adaptable to a body surface and can adapt to bumps, bends or depressions in the body surface. The sensor pad can also be compressible, so that the contact surface allows itself to be pressed into irregularities of the body surface, for example. The sensor pad can be made e.g. of foam, such as closed-pore foam material or neoprene. Foam ensures bendability, and offers a pleasant wearing comfort for a patient. Furthermore the receptacle of the sensor unit is also designed at least partially flexible, so that the lower side of the sensor unit can also be adapted to the body surface. Through the flexibility, or bendability, of the sensor pad and the receptacle the contact between the measuring device and the body surface for the transmission of light and measurement signals is improved and the wearing comfort of the measuring device increased for a patient. Preferably the covering is also designed flexible, so that it can adapt to the contour of the upper side of sensor pad and sensor unit. Since, according to the invention, the covering is not put on the sensor pad with the sensor received therein until this sensor pad is fixed e.g. with the adhesive layer on the body surface, the covering can adapt to the shape thereof as it has been predetermined by the body surface.

In an embodiment, the sensor pad can have on its outer periphery a plurality of indentations and/or thin places. Preferably the indentations and/or thin places are provided completely around the sensor pad. The indentations and/or thin places can be present e.g. at regular intervals. In regions in which a particular bendability of the sensor pad is necessary, the indentations and/or thin places can be provided more densely. The indentations can be provided e.g. as slits or round notches. The thin places can be formed by areas in which the sensor pad is thinner than in other areas. For example the thin places can be achieved through material cavities on the upper side of the sensor pad. The lower side of the sensor pad preferably <has> a uniform flat surface in order to ensure a secure resting on the body surface. The indentations and thin places make possible an easy adaptation of the sensor pad to the contour of a body surface.

In another embodiment of the measuring device according to the present invention, disposed on the lower side of the sensor pad at least on the contact surface is at least in some areas a detachable or respectively replaceable attachment layer in the form of a transparent adhesive layer, as mentioned above. Preferably the adhesive layer extends over the entire contact surface and in an especially preferred way over the entire lower side of the measuring device, i.e. over the entire contact surface of the sensor pad and the lower side of the receptacle. The adhesive layer is designed in such a way that it adheres with the one side to sensor pad and sensor unit and with the other side to the body surface. The adhesive layer is preferably designed in a way detachable from the sensor pad or respectively removable or renewable. The adhesive layer can be provided e.g. as a fabric layer prepared with an adhesive or a prepared foil. In addition to the adhesive layer a gel, a cream or a sprayable agent or the like can be provided that enables or improves the adhesive quality. After the carrying out of a measurement, the adhesive layer is preferably removed from the measuring device, and for another measurement a new or respectively another adhesive layer is provided between the lower side of sensor pad and sensor unit and body surface. A second adhesive layer can also be provided however over the first adhesive layer, so that the measuring device can be fastened again to the body surface with the second adhesive layer.

In another embodiment of the measuring device according to the present invention a control unit is provided which registers a background lighting in direction of the body surface between individual laser pulses of laser light sources of the sensor arrangement. The control unit can be provided internally inside of the receptacle of the sensor unit. Alternatively the control unit can be provided as an external unit which is connected to the sensor surfaces e.g. via conducting lines of the sensor unit. With this embodiment the sensor surfaces can serve both for measurement of parameters of the bodily tissue and for measurement of the background lighting. Preferably during emission of laser pulses, or respectively during the receiving of light reflected or scattered on the bodily tissue, i.e. the light to be measured, all the light falling on the sensor surfaces is detected. Thus both the background lighting and the light to be measured will be registered. For determining the light to be measured, and thereby for determining the measurement parameters, a value for the background lighting measured before the emission of a laser pulse is subtracted from the total incident light.

Furthermore the detected background lighting is used in order to achieve an emergency switching off for the measuring device. As soon as the value for the background lighting exceeds a predetermined maximal value, all light sources are switched off in order to ensure that these light sources do not represent any danger in the case where the measuring device is intentionally or unintentionally removed from the body surface.

In still another embodiment of a measuring device according to the present invention, on the one hand the light beamed by the light source is determined by the control unit. On the other hand, the light beamed by means of an additional light emission, independent thereof, can be registered. Through these two steps an emission of too high light energy can be prevented. For example, the laser power can be readjusted at any time via the laser diode power.

The two aforementioned embodiments of a measuring device represent independently of an above-described arrangement of the sensor unit and the sensor pad an advantageous further development of known measuring devices for measuring cerebral parameters. The right is therefore reserved to direct an own patent application to these aspects of the present invention.

In the following a method for preparation of a measuring device for non-invasive measuring of parameters of a bodily tissue according to the present invention will be described. Preferably used thereby is a measuring device of the above-described type. For preparation of the measuring device a sensor unit is inserted into a cutout of a sensor pad. Then an adhesive layer is put on at least the lower side of the sensor pad. The unit consisting of sensor pad and sensor unit is fixed with the adhesive layer to the body surface. Following the fixing of the unit of sensor pad and sensor unit to the body surface the cutout is covered, respectively closed, by putting a covering on an upper side of the sensor pad (8).

The sensor mat, the sensor unit and the covering are detachable from one another so that the covering can be taken off the sensor pad and sensor unit without having to remove the sensor pad and sensor unit from the body surface. Furthermore the sensor unit can be taken out of the cutout of the sensor pad without taking the sensor pad off the body surface. The sensor unit can thereby be removed from the patient, e.g. when it is supposed to be available for other measuring procedures or applications. The sensor pad can thereby remain on the body surface and marks the place of the measurement. If a sensor unit is again inserted into the sensor pad, it is ensured that the parameter measurement can be continued at the same place. Hence, after a removal of the covering, the sensor unit can be taken out of the sensor pad while the sensor pad remains fixed to the body surface. Then a sensor unit can be inserted again into the sensor pad remaining on the body surface and the cutout closed with another covering.

The adhesive layer is preferably provided on a lower side of the sensor pad, and is brought into contact with the body surface at least partially on a contact surface of the sensor pad. The contact surface thereby surrounds the sensor unit at least partially. Preferably the adhesive layer is applied over the entire lower side of the sensor pad and the sensor unit, while the contact surface completely surrounds the sensor unit. If the sensor pad with the inserted sensor unit is adhered to the body surface with the adhesive layer, sensor pad and sensor unit can adapt to the body surface. During subsequent putting on of the covering, this covering again adapts to the surface contour of the upper side of sensor pad and sensor unit. The covering can be fixed e.g. by means of an adhesive layer or detachable sticky layer.

Then the parameters of the bodily tissue are registered by means of the sensor unit. With the method according to the invention, through the covering over the entire under surface of the sensor unit, a steady pressure and/or a pressure constant over the surface is generated between sensor unit and body surface. Thus the sensor arrangement elements disposed on the under surface of the sensor unit, such as measuring surfaces and light outlets, are pressed with constant pressure on the body surface.

With the method according to the present invention a reliable, homogeneous contact between the sensor unit and the body surface is established so that the quality of the detected measuring results is improved.

If no further measures of cerebral parameters are foreseen, the sensor pad and the adhesive layer are also finally removed from the body surface. The sensor pad is then disposed of or cleaned, and the sensor unit can be made available, with another sensor pad, for a further parameter measurement. In principle of course the measuring device as a whole can be removed, i.e. sensor pad, sensor unit, covering and adhesive layer as one unit.

BRIEF DESCRIPTION OF THE FIGURES

A preferred embodiment of the invention is presented in the following with reference to the drawings, which serve merely explanatory purposes and are not to be interpreted in a limiting way. Features disclosed by the drawings should be considered as belonging to the disclosure of the invention individually and in any combination.

DETAILED DESCRIPTION OF VARIOUS EMBODIMENTS

In the following description of a measuring device according to the present invention a lower side should be understood as a side turned toward a body surface and an upper side should be understood as a side opposite the lower side. Upper and lower sides are thereby substantially at least close to parallel to a body surface. Peripheral surfaces are substantially perpendicular to upper and lower sides, or respectively to the body surface. A thickness is indicated in a direction perpendicular to an upper or respectively lower side, and a width is indicated parallel to these sides.

Figure 1:
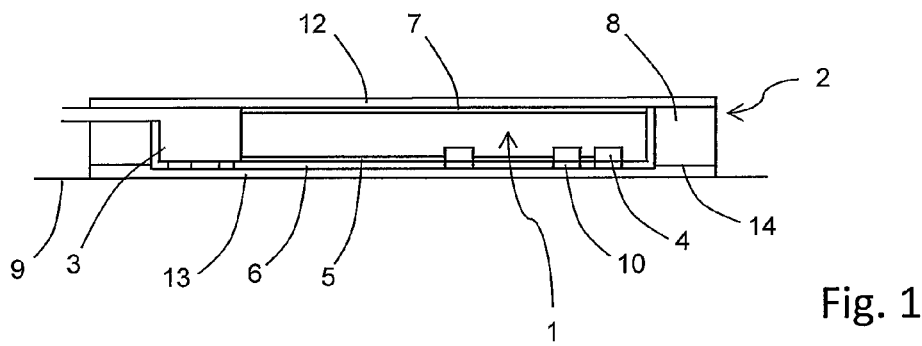
FIG. 1 shows a diagrammatic representation as sectional view through a measuring device according to the present invention.

Shown in FIG. 1 is diagrammatically the structure of a measuring device according to the invention for non-invasive measurement of parameters of a bodily tissue with a sensor unit 1 and a sensor pad 8 for detachable attachment of the measuring device on a body surface 9.

In this embodiment the measuring device consists substantially of two units: a reusable sensor unit 1 and a support unit 2. The reusable sensor unit 1 has a sensor arrangement with a light source 3, sensor surfaces 4 spaced apart thereto and optical conductors 5. Further elements can be provided in the sensor arrangement. The light source 3 consists of four different laser diodes, which emit light in the near-infrared spectroscopy (NIRS) range, each with differing wavelength, and are preferably switch on and off in a time-staggered way, for measurement of parameters. Used as sensor surfaces 4 are e.g. photodiodes. The sensor arrangement is accommodated inside an elongated, flat receptacle 6 with defined outer contour, the outer contour being adapted to the individual elements of the sensor arrangement. As can be seen from FIG. 3, the receptacle 6 is open on an upper side and has on a lower side a base area with a plurality of openings 10, among other things for the passage of light. The base serves as measuring surface 15, and is turned toward the body surface 9. The upper side is closed off with a lightproof closing cover 7. The receptacle 6 is designed to be flexible in order to be able to adapt to the contour of the body surface 9. The receptacle 6 is therefore bendable, and can assume e.g. a concave or convex shape.

The support unit 2 is provided as a single-use unit, and is disposed of after being used one time. Alternatively the support unit can also be used multiple times. The support unit 2 has a sensor pad 8, which is made e.g. of foam. The sensor pad 8 has an inner cutout 11 which forms a passage through the sensor pad 8 and corresponds to the outline of the outer contour of the receptacle 6. A covering 12 is put on the sensor pad 8 over the entire surface. On the lower side the sensor pad 8 has a contact surface 14 for resting on the body surface 9. Owing to the design of the cutout 11, the contact surface 14 is substantially annular, and surrounds the sensor unit 1 completely when this sensor unit is inserted in the sensor pad 8. Alternatively the contact surface could surround the sensor unit 1 only in some areas. It is however to be ensured that the sensor unit 1 is held securely in the cutout 11. The sensor pad 8 protrudes laterally with a width on the average of 5 mm beyond the periphery of the receptacle 6. The width determines the size of the contact surface 14 and thereby the contact on the body surface for fixing the measuring device. Disposed on the contact surface 14 is a removable adhesive layer 13. Furthermore the adhesive layer 13 extends over the measuring surface 15 of the sensor unit 1. By means of a sticky layer the covering 12 is attached in a detachable way on the upper surface of the sensor pad 8 which surrounds the receptacle 6. The sticky layer can thereby be provided only over the sensor pad or over sensor pad and sensor unit.

The covering 12 acts as stop for the sensor pad 8 when the measuring device with the lower side of receptacle 6 and sensor pad 8 sits firmly on the body surface 9, so that a constant and even pressure is generated between reusable sensor unit 1 and body surface 9. Owing to the abutting on the covering 12, the receptacle 6 cannot thereby move inside the cutout 11 out of the sensor pad 8 in direction of the covering.

Provided in the receptacle 6 is a control unit, which among other things controls the operations of the sensor arrangement. Via the sensor surfaces 4 the control unit automatically measures a background lighting in front of the lower side of the measuring device. The background lighting is measured in each case between the laser light pulses of the light source 3. During the laser light pulses the total light of the light source 3 is measured and then the previously measured background lighting is subtracted therefrom. If a measuring device becomes loose or falls off, the background lighting changes and all laser diodes of the light source 3 are automatically switched off as soon as the background lighting exceeds a predetermined value. Furthermore in the control unit the electric current through the laser diodes is measured. In addition via a further optical emission (not shown) the actual emitted light is determined. Through the measured electric current and the determination of the emitted light an emission of too high laser light energy can be avoided. The laser power can be readjusted at any time via the laser diode power. The control unit can be calibrated after assembly with respect to the optical power of the laser diode and the linearity. The calibration can be repeated regularly, if necessary. The conductors 5 inside the receptacle 6 have an EMI shielding in order to prevent inaccurate measurement results.

Figure 2:
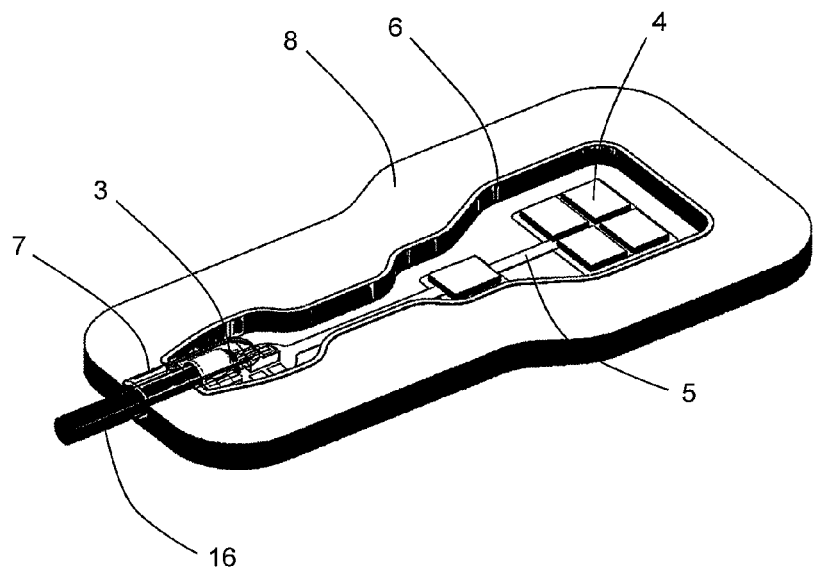
FIG. 2 shows a measuring device according to the present invention with a sensor unit and a sensor pad in a three-dimensional representation.

Shown in FIG. 2 is a three-dimensional view of the measuring device, the sensor unit 1 being inserted in the sensor pad 8. The outer contour of the receptacle 6 abuts on the inner circumference of the sensor pad 8. A feeder 16 protrudes laterally out of the receptacle 6 and the sensor pad 8. The feeder 16 is borne in the sensor pad in a recess 17, so that the contact surface is not interrupted (see FIG. 5). The feeder serves the providing and receiving of electrical or optical signals, the power supply and the connection to an external control and processing unit and/or a control unit. The receptacle 6 terminates on the upper side and the lower side in a substantially flush way with respect to the upper side and the lower side of the sensor pad 8, so that a covering 12 with a flat lower side can be fixed on the upper side.

Figure 3:
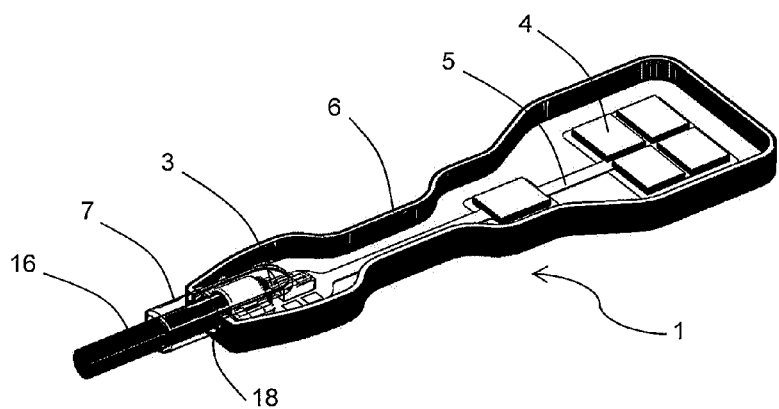
FIG. 3 shows a detailed view of the sensor unit of the measuring device according to FIG. 2.

Shown in FIG. 3 in a schematic three-dimensional representation, as mentioned above, is a sensor unit 1 according to the present invention. Accommodated in the sensor unit 1 is a sensor arrangement having a light source 3, sensor surfaces 4 and conductors 5. The receptacle 6 is designed as a kind of flat housing or shell with a base area and a peripheral walling. The peripheral walling has a passage 18 for the feeder 16. The passage 18 is open upward so that the feeder 16 can be easily placed in. The closing cover 7 extends over the inner space and partially over the feeder 17 <sic. 16>.

Figure 4:
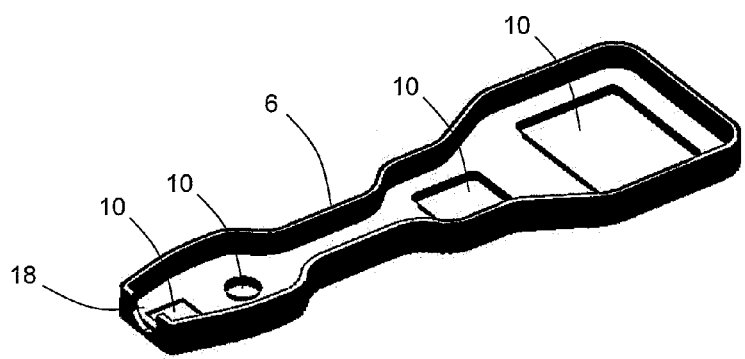
FIG. 4 shows a receptacle of a sensor unit according to FIG. 3.
Figure 5:
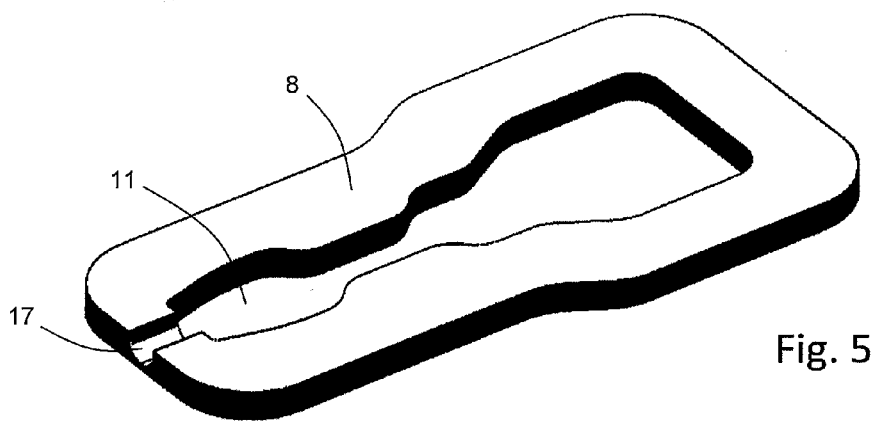
FIG. 5 shows a detailed view of the sensor pad of the measuring device according to FIG. 2.

Shown in FIG. 4 is the receptacle 6 without further elements. The base area, which forms the base for the measuring surface 15, has a plurality of openings 10, over which the elements of the sensor arrangement are provided, for example the sensor surfaces 4 and the light source 3. Shown in FIG. 5 is the support unit 2 in the form of the sensor pad 8 without inserted sensor unit 1. The sensor pad 8 is designed as an elongated flat pad. From this the inner contour of the cutout 11 is visible, which corresponds to the outer contour of the receptacle 6. The width of the sensor pad 8 from the rim of the cutout 11 to the outer peripheral side is at least approximately the same around the cutout with slight deviations in regions in which the outer contour of the receptacle 6 varies greatly. The arrangement of the recess 17 in the sensor pad 8 corresponds to the arrangement of the passage 18 in the receptacle 6. The sensor pad 8 is provided as foam element which can be manufactured in large numbers simply and economically. The support unit 2 can therefore be provided as single-use disposable unit.

REFERENCE NUMERALS

1 sensor unit
2 support unit
3 light source
4 sensor surface
5 conductor
6 receptacle
7 closing cover
8 sensor pad
9 body surface
10 opening
11 cutout
12 covering
13 adhesive layer
14 contact surface
15 measuring surface
16 feeder
17 recess
18 passage

The invention claimed is:

1. Measuring device for non-invasive measurement of parameters of a bodily tissue, said measuring device comprising
   a sensor unit (1); and
   a sensor pad (8) for detachable placement of the measuring device on a body surface,
   wherein:
      the sensor unit (1) has a receptacle (6), the interior space of which accommodates a sensor arrangement, the receptacle (6) having a measuring surface (15) in the direction of the body surface,
      the sensor pad (8) has an inner cutout (11) for accommodating the sensor unit (1) and a lower contact surface (14), at least partially surrounding the sensor unit (1), for placement on the body surface (9),
      the measuring surface (15) and the lower contact surface (14) lie in a single plane,
      the cutout (11) forms a passage through the sensor pad (8),
      a covering (12) is provided for closing the cutout (11) over an upper side of the sensor unit (1) and the sensor pad (8) during a measurement of parameters, and
      the sensor unit (1), the sensor pad (8) and the covering (12) are detachable from one another.

2. Measuring device according to claim 1, wherein the surface of the covering (12) corresponds substantially to the size of the upper side of the sensor pad (8).

3. Measuring device according to claim 1, wherein a transparent adhesive layer (13) is provided over a lower side of sensor unit (1) and sensor pad (8) for fixing the measuring device to a body surface (9).

4. Measuring device according to claim 1, wherein the receptacle (6) is at least partially open toward the upper side and is closed with a lightproof closing cover (7).

5. Measuring device according to claim 4, wherein the closing cover (7) is formed by a sealing which seals the sensor arrangement in the interior space of the receptacle (6).

6. Measuring device according to claim 1, wherein the receptacle (6) abuts on an inner side of the covering (12) and an inner side of the adhesive layer (13).

7. Measuring device according to claim 1, wherein the contact surface (14) of the sensor pad (8) in the area in which it surrounds the sensor unit (1) is at least 5 mm wide.

8. Measuring device according to claim 1, wherein the sensor pad (8), the receptacle (6) and the covering are designed at least partially flexible.

9. Measuring device according to claim 1, wherein the sensor pad (8) has on its outer periphery a plurality of indentations and/or thin places.

10. Measuring device according to claim 1, wherein the shape of the cutout (11) matches the outer contour of the sensor unit (1) in a form-fitting fashion.

11. Measuring device according to claim 1, wherein the sensor unit (1) is provided as reusable unit, whereas sensor pad (8) and the covering (12) are provided as disposable articles.

12. Measuring device according to claim 1, wherein a control unit is provided which registers a background lighting in direction of the body surface (9) between laser pulses of laser light sources of the sensor arrangement.

13. Measuring device according to claim 1, wherein it is provided as a kit with a plurality of elements to be put together, the sensor unit (1) being provided as reusable element, and sensor pad (8) and covering (12) being supplied in a packaging and being provided as disposable articles.

14. Method of preparing a measuring device for non-invasive measurement of parameters of a bodily tissue, said method comprising the steps of:
   inserting a sensor unit (1) having a measuring surface (15) into an inner cutout (11) of a sensor pad (8) having a lower contact surface (14), whereby the cutout (11) forms a passage through the sensor pad (8), and whereby the measuring surface (15) and the lower contact surface (14) lie in a single plane;
   attaching an adhesive layer at least to the lower side of the sensor pad (8);

fixing the unit of sensor pad (8) and sensor unit (1) to the body surface (9) with the adhesive layer; and covering the cutout (11) by putting a covering (12) on an upper side of the sensor pad (8) subsequent to the attachment of the unit of sensor pad (8) and sensor unit (1) to the body surface (9).

15. Method according to claim 14, wherein at least one of a steady or a constant pressure is generated between sensor unit (1) and body surface (9) by the covering (12).

16. Method according to claim 14, wherein, after removal of the covering (12), the sensor unit (1) is taken out of the sensor pad (8) while the sensor pad (8) remains attached to the body surface (9) and then another sensor unit (1) is inserted into the sensor pad (8) remaining on the body surface (9) and the cutout (11) is closed with a further covering (12).

17. Method according to claim 14, wherein, after a carrying out of a parameter measurement the sensor unit (1) is removed from the sensor pad (8), the sensor pad (8) is disposed of or is cleaned and the sensor unit (1) with another sensor pad (8) and a further covering (12) is made available for another parameter measurement.

\* \* \* \* \*